US012590141B2

(12) United States Patent
Chen et al.

(10) Patent No.: US 12,590,141 B2
(45) Date of Patent: Mar. 31, 2026

(54) MONOCLONAL ANTIBODIES AGAINST HENIPAVIRUS GLYCOPROTEIN G AND ENCODING NUCLEIC ACIDS THEREOF

(71) Applicant: ACADEMY OF MILITARY MEDICAL SCIENCE, PLA, Beijing (CN)

(72) Inventors: Wei Chen, Beijing (CN); Changming Yu, Beijing (CN); Yujiao Liu, Beijing (CN); Pengfei Fan, Beijing (CN); Guanying Zhang, Beijing (CN); Yaohui Li, Beijing (CN); Jianmin Li, Beijing (CN); Xiangyang Chi, Beijing (CN); Meng Hao, Beijing (CN); Ting Fang, Beijing (CN); Yunzhu Dong, Beijing (CN); Xiaohong Song, Beijing (CN); Yi Chen, Beijing (CN); Shuling Liu, Beijing (CN)

(73) Assignee: Academy of Military Medical Science, PLA, Beijing (CN)

( * ) Notice: Subject to any disclaimer, the term of this patent is extended or adjusted under 35 U.S.C. 154(b) by 584 days.

(21) Appl. No.: 18/005,979

(22) PCT Filed: Jun. 27, 2021

(86) PCT No.: PCT/CN2021/102588
§ 371 (c)(1),
(2) Date: Jan. 19, 2023

(87) PCT Pub. No.: WO2022/017124
PCT Pub. Date: Jan. 27, 2022

(65) Prior Publication Data
US 2024/0294614 A1      Sep. 5, 2024

(30) Foreign Application Priority Data
Jul. 22, 2020      (CN) .......................... 202010713274.0

(51) Int. Cl.
*A61P 31/14*            (2006.01)
*C07K 16/10*            (2006.01)

(52) U.S. Cl.
CPC .............. *C07K 16/10* (2013.01); *A61P 31/14* (2018.01); *C07K 16/1027* (2013.01); *C07K 2317/24* (2013.01); *C07K 2317/33* (2013.01); *C07K 2317/76* (2013.01); *C07K 2317/92* (2013.01)

(58) Field of Classification Search
CPC ..... A61P 31/14; C07K 16/10; C07K 16/1027; C07K 2317/24; C07K 2317/33; C07K 2317/76; C07K 2317/92; C07K 2317/21; C07K 2317/52; C07K 2317/565
See application file for complete search history.

(56) References Cited

FOREIGN PATENT DOCUMENTS

| CN | 106163560 A | 11/2016 |
| CN | 110028579 A | 7/2019 |
| WO | 2006137931 A2 | 12/2006 |
| WO | 2012149536 A1 | 11/2012 |

*Primary Examiner* — Robert S Landsman
(74) *Attorney, Agent, or Firm* — Fox Rothschild LLP

(57) ABSTRACT

Provided is an anti-Henipavirus monoclonal antibody having broad spectrum neutralization activity, wherein the antibody comprises a macaque variable region and a human constant region. The antibody of the present invention has good binding activity to both Nipah virus glycoprotein G and Hendra virus glycoprotein G, can effectively neutralize Nipahpseudovirus and Hendra pseudovirus, and can be used for preparing drugs for treating Henipavirus diseases.

9 Claims, 10 Drawing Sheets

Specification includes a Sequence Listing.

MONOCLONAL ANTIBODIES AGAINST HENIPAVIRUS GLYCOPROTEIN G AND ENCODING NUCLEIC ACIDS THEREOF

CROSS-REFERENCE TO RELATED APPLICATIONS

This application is the U.S. national phase of International Patent Application No. PCT/CN2021/102588, filed on Jun. 27, 2021, which claims priority to Chinese Patent Application No. 202010713274.0, filed on Jul. 22, 2020, the contents of which are incorporated herein by reference in their entirety.

REFERENCE TO A SEQUENCE LISTING

This application incorporates by reference the Sequence Listing submitted in Computer Readable Form as file SeqList_176495-00800, created on Jun. 7, 2023 and containing 20,029 bytes.

TECHNICAL FIELD

The invention discloses a group of monoclonal antibodies, which belongs to the field of immunology and microbiology.

BACKGROUND TECHNOLOGY

Nipahvirus (NiV) and Hendra virus (HeV) are single negative-stranded RNA viruses, belonging to the genus Henipavirus of the family Paramyxoviridae. NiV and HeV are zoonotic viruses that can be infected by direct contact and can cause fatal respiratory and neurological diseases. The natural hosts of NiV and HeV are both fruit bats, but their transmission routes are slightly different. HeV is currently only found in the fruit bat-horse-human transmission route, while NiV can be transmitted through fruit bat-pig-human transmission and can also be directly transmitted to human from bats or from human itself.

The outbreak caused by HeV first appeared in 1984 in the town of Hendra, a suburb of Brisbane, Australia. A total of 21 horses and two people were infected in this outbreak. Horses are identified as intermediate hosts because people who care for or necropsy sick or dead horses are susceptible. Subsequent outbreaks have also occurred on Australia's east coast, causing seven people infected and four died in 2006, and leading to 23 horses and a dog died, and more than 60 people infected in 2011.

NiV was first discovered in Malaysia. From September 1998 to April 1999, a number of pig farm staffs died from severe encephalitis and a large number of pigs died of illness in Perak, Malaysia. It was initially thought to be a Japanese encephalitis virus infection, but it was later found that this outbreak was significantly different from Japanese encephalitis in terms of susceptible population, infection rate, and infection mode. In addition, many of the patients had been vaccinated against Japanese encephalitis, so the researchers identified this as a new infectious disease. In this outbreak, both people and livestock showed acute respiratory syndrome, resulting in 256 infections, 105 deaths, and 1.16 million pig deaths. The epidemic further spread to a slaughter house in Singapore, causing 2,511 workers infected, and 1 died. In October 1999, researchers isolated the virus from the cerebrospinal fluid of a patient. Shortly afterward, NiV was isolated from the urine of Malaysian fruit bat, the natural host of NiV was identified. Subsequently, Nipah virus disease has been reported in India, Cambodia, Thailand and other countries. In recent years, Nipah virus disease has occurred many times in Bangladesh and India, causing hundreds of deaths, with a mortality rate of 50% to 100%. Studies on NiV have mainly focused on the Malaysia strain (NiV-MY) and the Bangladesh strain (NiV-BD).

Technical Problem

During the process of invading host cells, Henipavirus binds to the receptor ephrin-B2/B3 through the viral surface glycoprotein G, which will activate the conformation change of fusion glycoprotein F, thereby mediate the fusion of the viral membrane and the cell membrane, and finally enable the viral genome to entry the cell. NiV and HeV have highly similar gene sequences, and the amino acid sequence similarity of proteinG and protein is 83% and 89%, respectively. Therefore, both protein G and protein F are important targets in vaccine and antiviral drug development. There is currently no vaccine available for human use. As for drugs, only one monoclonal antibody, m102.4, has entered clinical trials. M102.4 is a human monoclonal antibody screened from recombinant human Fab phage display library, and can potently neutralize NiV and HeV. In challenge protection experiments in ferrets and African green monkeys, m102.4 can achieve effective protection after Henipavirus challenge. In 2010, m102.4 was administered as an emergency protective drug in two individuals at high risk of exposure, neither of whom developed symptoms of infection.

In view of the technical demand for therapeutic antibodies against Henipavirus in the art, the purpose of the invention is to provide candidate monoclonal antibodies targeting unique epitopes on protein G, and then provide its application in the preparation of a medicine for the treatment of Henipavirus infections.

Technical Solutions

Based on the above purpose, the invention firstly provides specific neutralizing antibody against Henipavirus glycoprotein G. The antibody is monoclonal antibody, and the amino acid sequence of CDR (complementarity determining region) 1, CDR2, CDR3 of the heavy chain variable region of the said antibody and the amino acid sequence of CDR1, CDR2, CDR3 of the light chain variable region of the said antibody are shown respectively as the following sequence combinations:

26-33, 51-58, 97-116 of SEQ ID NO: 1 and 27-36, 54-56, 93-100 of SEQ ID NO:3, or 26-33, 51-58, 97-117 of SEQ ID NO:5 and 27-32, 50-52, 89-97 of SEQ ID NO:7, or 26-33, 51-58, 97-115 of SEQ ID NO:9 and 27-32, 50-52, 89-97 of SEQ ID NO:11, or 26-33, 51-58, 97-109 of SEQ ID NO:13 and 27-37, 10 51-53, 90-100 of SEQ ID NO:15.

In a preferred embodiment, the amino acid sequence of the heavy chain variable region of the said antibody and the amino acid sequence of the light chain variable region of the said antibody are respectively shown as any combination of the following sequences:

SEQ ID NO: 1 and SEQ ID NO:3 (in the invention, the antibody with these variable regions is named as "1B6"), or SEQ ID NO:5 and SEQ ID NO:7 (in the invention, the antibody with these variable regions is named as "1E5"), or SEQ ID NO:9 and SEQ ID NO: 11 (in the invention, the antibody with these variable regions is named as "2A4"), or SEQ ID NO:13 and SEQ ID NO:15 (in the invention, the antibody with these variable regions is named as "2E7").

In a more preferred embodiment, the amino acid sequence of the heavy chain constant region of the said antibody is shown as SEQ ID NO:17, and the amino acid sequence of the light chain constant region of the said antibody is shown as SEQ ID NO: 19 or SEQ ID NO:21.

Secondly, the invention also provides an isolated nucleic acid encoding the heavy chain and/or light chain of the said monoclonal antibody. The sequence of the isolated nucleic acid encoding the heavy chain variable region and/or the sequence of the isolated nucleic acid encoding the light chain variable region are respectively shown as any combination of the following sequences:

SEQ ID NO:2 and SEQ ID NO:4 (in the invention, the antibody with these variable regions is named as "1B6"), or SEQ ID NO:6 and SEQ ID NO:8 (in the invention, the antibody with these variable regions is named as "1E5"), or SEQ ID NO:10 and SEQ ID NO:12 (in the invention, the antibody with these variable regions is named as "2A4"), or SEQ ID NO:14 and SEQ ID NO:16 (in the invention, the antibody with these variable regions is named as "2E7").

In a preferred embodiment, the isolated nucleic acid encoding the heavy chain constant region is shown as SEQ ID NO: 18, and the isolated nucleic acid encoding the light chain constant region is shown as SEQ ID NO:20 or SEQ ID NO:22.

Thirdly, the invention also provides a functional element expressing the above-mentioned isolated nucleic acid encoding the heavy chain and/or light chain of the said monoclonal antibody.

In a preferred embodiment, the functional element is a linear expression cassette.

In another preferred embodiment, the functional element is a mammalian expression vector.

Fourthly, the invention also provides a host cell comprising the above functional elements.

In a preferred embodiment, the host cell is Expi293F cell.

In another preferred embodiment, the host cell is CHO-S cell. In the invention, CHO-S cell can be used to construct stable expression cell lines to realize industrial production.

Finally, the invention provides the application of the above-mentioned monoclonal antibodies in the preparation of the therapeutic drug for Henipavirus disease.

Technical Effect

The monoclonal antibodies against Henipavirus glycoprotein G in the invention are composed of monkey-derived variable region and human-derived constant region, and the monkey-derived light and heavy chains variable region have unique CDR regions. Antibodies disclosed in the invention exhibit excellent broad-spectrum capacity of binding with antigen, and can effectively bind with Nipah virus and Hendra virus glycoprotein G. The antibodies can potently neutralize the pseudotyped Nipah virus and Hendra virus. The neutralizing capacity of the antibody increases with the increase of antibody concentration, and nearly 100% inhibition against Nipah and Hendra pseudoviruses could be achieved at a concentration of 1 µg/mL. The above excellent technical effect shows the monoclonal antibodies in the invention can be used in the preparation of the therapeutic drug for Henipavirus disease.

EXAMPLES

Figure 1:
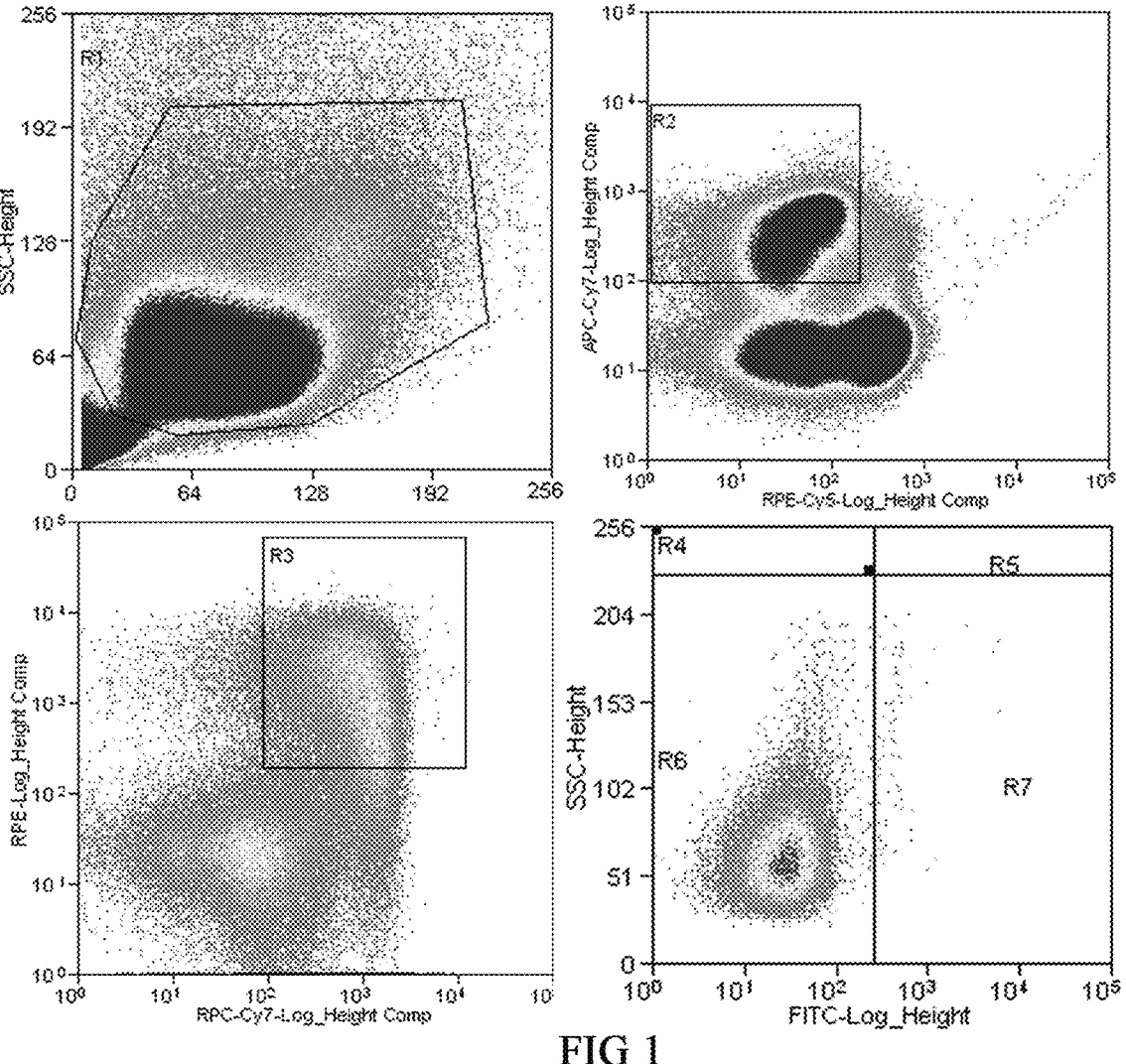
FIG. 1. Sorting of rhesus monkey memory B cells.

The invention is further described below with reference to specific embodiments, and the advantages and characteristics of the invention will become clearer with the description. However, these embodiments are only exemplary, and do not constitute any limitation on the protection scope defined by the claims of the invention.

Example 1. Screening and Preparation of Antibodies

1. Collection of Blood Samples

Female rhesus monkeys were immunized with adenovirus vector Nipah virus candidate vaccine, recombinant NiV G protein and recombinant HeV G protein three times by intramuscular injection on day 0, 28, and 49, respectively. Finally, blood samples of the rhesus monkey were collected on day 77.

2. Labeling of NiV-BD G with FITC

The NiV-BD G was labeled with fluorescein isothiocyanate (FITC) to sort antigen-specific memory B cells. Method is described as below:

1) FITC (SIGMA, F4274) is dissolved in dimethyl sulfoxide at a final concentration of 20 mg/mL. Take 100 µL of NiV-BD G (about 3.3 mg/mL) and add carbonate buffer (pH=9.6) to 400 µL.

2) Add 8 UL FITC to the NiV-BD G solution and incubate for 3 h at 4° C. in the dark.

3) Buffer-exchange the protein into PBS using a 30 kDa centrifugal concentrator tube until the filtrate is transparent and colorless. Wrap the labeled protein in tin foil paper and store it at 4° C. until use.

3. Flow Sorting of Memory B Cells

PBMCs are isolated from blood samples using a Ficoll density gradient centrifugation method, details are described as follows:

1) Take fresh EDTA anticoagulant whole blood and dilute the whole blood with the same volume of PBS.

2) Add the separation solution to the centrifuge tube, and slowly spread the diluted blood sample above the surface of the separation solution to keep the interface between the two liquid surfaces clear. Separation solution, anticoagulated blood, PBS (or normal saline) volume is 1:1:1.

3) After Balancing, the tube is centrifuged at 800×g, 3rd gear acceleration and deceleration, room temperature, for 30 min. After centrifugation, the bottom of the tube is red blood cells, the middle layer is the separation solution, the top layer is the plasma/tissue homogenate layer. The thin and dense white film between the plasma layer and the separation solution layer is mononuclear cells (including lymphocytes and monocytes). Carefully pipette the mononuclear cells into another centrifuge tube.

4) Dilute the cells with PBS and gently invert and mix well. The tube is centrifuged at 300×g, room temperature, for 10 min. Discard supernatant and repeat twice. Finally, the lymphocytes are resuspended in PBS for later use.

5) Count 5×10⁵ cells in a volume of 50 μL PBS, add the five fluorescent dyes recommended in the following table, and incubate for 1 h at 4° C. in the dark.

TABLE 1

| | | Fluorescent dyes used for cell sorting | | |
|---|---|---|---|
| Marker | Fluorescence | Company/Cat. No. | Volume |
| Antigen | FITC | SIGMA, F4274 | 4 μg |
| IgG | PE | BD, 555787 | 15 μL |
| CD19 | APC-AF 700 | Beckman, IM2470 | 5 μL |
| CD3 | PerCP | BD, 552851 | 10 μL |
| CD27 | PC7 | Beckman, A54823 | 10 μL |

6) Wash cells 2-3 times with PBS containing 2% FBS and resuspend in 400 μL FPBS. Remove cell clusters with a 40 μm cell filter, and store at 4° C. in the dark for sorting.

7) NiV-BD G-specific single memory B cells are sorted by a cell sorter (Beckman, MoFlo XDP) using a strategy of IgG⁺/CD3⁻/CD19⁺/CD27⁺/NiV-BD G⁺. Each single cell is directly sorted into 96-well plates contains 20U RNase inhibitor and 20 μL RNase free water in each well. Store plates at −80° C. Cell sorting result is shown in FIG. 1. Cells circled by R7 box in the figure are characterized by IgG⁺/CD3⁻/CD19⁺/CD27⁺/NiV-BD G⁺, which are NiV-BD G-specific memory B cells.

4. Amplification of Antibody Genes by Single Cell PCR

1) Reverse Transcription PCR

A total of 1124 NiV-BDG-specific memory B cells were obtained by flow sorting. The SuperScript III reverse transcription kit was used to perform reverse transcription polymerase chain reaction (PCR). The mixed system was prepared according to the instructions and directly added to 96-well plates containing single cells for PCR reaction. Reaction conditions: 42° C., 10 min; 25° C., 10 min; 50° C., 60 min; 94° C., 5 min. The reaction system and conditions are described as follows.

TABLE 2

| | |
|---|---|
| Reaction system for reverse transcription PCR | |
| Component | Volume |
| Template (sorted single cells) | 20 μL |
| Random primer | 3 μL |
| dNTP | 1 μL |
| 10× buffer | 3 μL |
| 0.1M DTT | 1 μL |
| MgCl₂ | 2 μL |
| RNaseOUT | 1 μL |
| SuperScript III | 0.5 μL |

2) Nested PCR

Reverse transcription products were used as the template, and two rounds of nested PCR reactions were performed to amplify H, K, and A genes. The detail process is described as follows.

The first-round nested PCR reaction system is listed in Table 3.

TABLE 3

| | |
|---|---|
| The reaction system for the first-round of nested PCR | |
| Component | Volume |
| Template (Reverse transcription products) | 1 μL |
| Mixed primers (H/κ/λ) | 1.5/1/1 μL |
| dNTP | 2 μL |
| 10× buffer | 2.5 μL |
| TransStart Taq DNA polymerase | 0.5 μL |
| RNase-free water | to 25 μL |

The first-round of nested PCR reaction conditions: firstly pre-denaturation 5 min at 95° C.; then 40 cycles of denaturation 30 s at 95° C., annealing 30 s at 57° C., elongation 45 s at 72° C.; finally elongation 10 min at 72° C.

The first-round nested PCR primers are listed in Table 4.

TABLE 4

| | |
|---|---|
| Primers for first-round nested PCR | |
| Primer | Sequence |
| 5'VH1.L1 | ATGGACTKGACCTGGAGG |
| 5'VH2.L1 | ATGGACACGCTTTGCTCC |
| 5'VH3A.L1 | ATGGAGTTKGGGCTGAGCTG |
| 5'VH3B.L1 | ATGGAGTTTGKRCTGAGCTGG |
| 5'VH3C.L1 | ATGGAGTCRTGGCTGAGCTGG |
| 5'VH3D.L1 | ATGGAGTTTGTGCTGAGTTTGG |
| 5'VH4.L1 | ATGAAGCACCTGTGGTTC |
| 5'VH5A.L1 | ATGGGGTCAACTGCCATC |
| 5'VH5B.L1 | ATGGGGTCCACCGTCACC |
| 5'VH6.L1 | ATGTCTGTCTCCTTCCTCA |
| 5'VH7.L1 | ATGGACCTCACCTGGAGC |
| 3'IgG(Outer) | GGAAGGTGTGCACGCCGCTGGTC |
| | |
| 5'VK1A.L1 | ATGGACATGAGGGTCCCCGC |
| 5'VK1B.L1 | GGCTCCTKCTGCTCTGGCTC |
| 5'VK2.L1 | ATGARGYTCCCTGCTCAG |
| 5'VK3.L1 | ATGGAARCCCCAGCWCAGC |
| 5'VK4.L1 | ATGGTGTCACAGACCCAAGTC |
| 5'VK5.L1 | ATGGCATCCCAGGTTCASC |
| 5'VK6A.L1 | ATGTTGTCTCCATCACAACTC |
| 5'VK6B.L1 | ATGGTGTCCCCATTGCAACTC |
| 5'VK7.L1 | ATGGGGTCCTGGGCTCC |
| 3'Kappa(Outer) | GTCCTGCTCTGTGACACTCTC |
| | |
| 5'VL1.L1 | ATGGCCTGGTYYCCTCTC |
| 5'VL2/7/10.L1 | ATGGCCTGGRCTCTGCTCC |
| 5'VL3A.L1 | ATGGCCTGGATTCCTCTC |
| 5'VL3B.L1 | ATGGCCTGGACCTTTCTC |
| 5'VL3C.L1 | ATGGCCTGGACCCCTCCC |

TABLE 4-continued

Primers for first-round nested PCR

| Primer | Sequence |
|---|---|
| 5'VL4A.L1 | ATGGCCTGGGTCTCCTTC |
| 5'VL4B.L1 | ATGGCCTGGACCCCACTC |
| 5'VL5/11.L1 | ATGGCCTGGACTCCTCTC |
| 5'VL6.L1 | ATGGCCTGGGCTCCACTCC |
| 5'VL8.L1 | ATGGCCTGGATGATGCTTC |
| 5'VL9.L1 | ATGGCCTGGGCTCCTCTG |
| 3'Lamda(Outer) | TGTTGCTCTGTTTGGAGGG |

The second-round nested PCR reaction system is listed in Table 5.

TABLE 5

The reaction system for the second-round of nested PCR

| Component | Volume |
|---|---|
| Template (Products of the first-round nested PCR) | 1.6 μL |
| Mixed primers (H/κ/λ) | 3.2/1.6/1.6 μL |
| dNTP | 3.2 μL |
| 10× buffer | 4 μL |
| TransStart Taq DNA polymerase | 0.8 μL |
| RNase-free water | to 40 μL |

The second-round nested PCR primers are listed in Table 6.

TABLE 6

Primers for second-round nested PCR

| | Primer | Sequence |
|---|---|---|
| H | 5'VH1A.SE | TGGCAGCAGCTACAGGTGC |
| | 5'VH1B.SE | TGACAGCAGCTACAGGCGC |
| | 5'VH1C.SE | TGGCAGCAGCAACAGGCAC |
| | 5'VH2.SE | GTCCCGTCCTGGGTCTTGTC |
| | 5'VH3A.SE | GCTGTTTGGAGAGGTGTCCAGTGTG |
| | 5'VH3B.SE | GCCATATTAGAAGGTGTCCAGTGTG |
| | 5'VH3C.SE | GCTCTTTTGAAAGGTGTCCAGTGTG |
| | H 5'VH3D.SE | GCTATTTTAAGAGGTGTCCAGTGTG |
| | 5'VH3E.SE | GCTATTTTAAAAGGTGTCCAGTGTG |
| | 5'VH4.SE | AGCTCCCAGATGGGTCYTGTCC |
| | 5'VH5.SE | GCTGTTCTCCARGGAGTCTGTG |
| | 5'VH6.SE | GGCCTCCCATGGGGTGTC |
| | 5'VH7A.SE | GCAGCAACAGGTGCCCACTC |
| | 5'VH7B.SE | GCAGCAACAGGCACCCACTC |
| | 3'IgG(Inner) | GTTCAGGGGAAGTAGTCCTTGAC |
| κ | 5'VK1/2.SE | CTCCCAGGTGCCAGATGTGA |
| | 5'VK1B.SE | GGTCCCTGGRTCCAGTGGG |
| | 5'VK3A.SE | TGGCTCCCAGGTACCACYGGA |
| | 5'VK3B.SE | TGGATCCCGGATGCCGCCG |
| | 5'VK3C.SE | TGGCTTCCGGATACCACTGGA |
| | 5'VK4.SE | CTGGATCTCTGGTGTCTGTGG |
| | 5'VK5.SE | CCTTTGGATCTCTGMTGCCAGG |
| | 5'VK6.SE | TGGGTTCCAGTCTCCAAGGG |
| | 5'VK7.SE | TGTGCTCCAGGCTGCAATGG |
| | 3'Kappa(Inner) | ATTCAGCAGGCACACAACAGAG |
| λ | 5'VL1A.SE | CTGTGCAGGGTCCTGGGCC |
| | 5'VL1B.SE | CTGCACAGGGTCCYGGGCC |
| | 5'VL2.SE | TCACTCAGGGCACAGGATCC |
| | 5'VL3A.SE | CGCCCTCTGCACAGTCTCTGTGG |
| | 5'VL3B.SE | CACTCTCTGCACAGGTTCCGTGG |
| | 5'VL4A.SE | TTCATTTTCTCCACAGGTCTCTGTG |
| | 5'VL4B.SE | CTTCACTGCAGAGGTGTCTCTC |
| | 5'VL5.SE | CACTGCACAGGTTCCCTCTC |
| | 5'VL6.SE | CTGCACAGGGTCTTGGGCTG |
| | 5'VL8.SE | GCTTATGGCTCAGGAGTGGA |
| | 3'Lamda(Inner) | AGACACACTAGTGTGGCCTTG |

The reaction conditions for the second-round of nested PCR are the same as those of the first-round of nested PCR.

3) Capillary Electrophoresis

Figure 2:
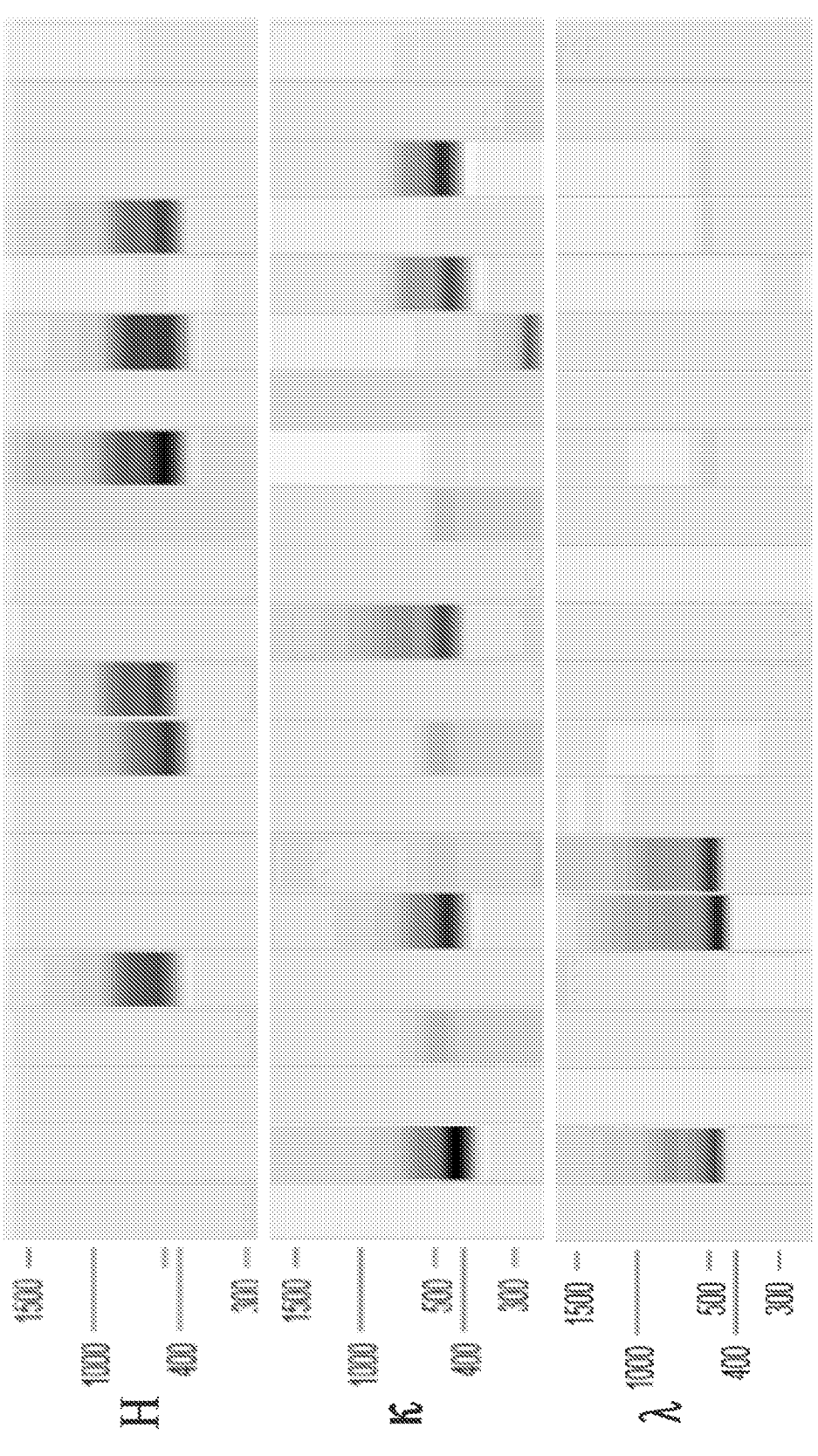
FIG. 2. Capillary electrophoresis of nested PCR products.

After the nested PCR, the amplified products were analyzed by capillary electrophoresis using the QIAxcel DNA Fast Analysis Cartridge. Positive clones with paired light and heavy chains were selected for sequencing, and the variable region sequences of the antibody were analyzed by Vector NTI software and IMGT website. The results of nested PCR capillary electrophoresis are shown in FIG. 2.

5. Expression of Antibodies Using Linear Expression Cassettes

Through the above single-cell PCR reaction, 254 paired antibody sequences were obtained, and the antibody was rapidly expressed by constructing linear expression cassettes.

Firstly, promoter-leader sequence fragments, constant region fragments (synthetized by Sangon Biotech, the heavy chain constant region sequence is shown as SEQ ID NO:17, the DNA coding sequence is shown as SEQ ID NO:18; the constant region sequence of the kappa light chain is shown as SEQ ID NO:19, the DNA coding sequence is shown as SEQ ID NO:20; the constant region sequence of the lambda light chain is shown as SEQ ID NO:21, and the DNA coding sequence is shown as SEQ ID NO:22), and poly A-tail fragments (Genbank accession number: X03896.1) were obtained by PCR. Then amplify the antibody variable region fragments, and the PCR reaction system is listed in Table 7.

TABLE 7

Reaction system for amplifying variable region fragments

| Component | Volume |
|---|---|
| Template (Products of the second-round nested PCR) | 0.5 μL |
| Mixed primers | 0.3 μL |
| dNTP | 2 μL |
| 10× buffer | 2 μL |
| TransStart Taq DNA polymerase | 0.25 μL |
| Deionized water | to 20 μL |

PCR reaction conditions: firstly pre-denaturation at 95° C. for 5 min; then 30 cycles of 95° C., 30 s; 60° C., 30 s; 72° C., 30 s; finally elongation at 72° C. for 10 min.

Take the amplified promoter-leader sequence fragment, constant region-poly A tail fragment and variable region fragment as templates, and use CMV-UP and TK-PolyA as primers, to perform overlapped extension PCR to amplify linear expression cassettes of H, κ and λ chains. PCR products were identified by nucleic acid electrophoresis. The reaction system for amplifying the full-length linear expression cassettes is listed in Table 8.

TABLE 8

Reaction system for amplifying full-length linear expression cassettes

| Component | Volume |
|---|---|
| Template 1 (promoter-leader sequence fragment) | 10 ng |
| Template 2 (constant region-poly A tail fragment) | 10 ng |
| Template 3 (variable region fragment) | 0.5 μL |
| Upstream primer (CMV-UP) | 2.5 μL (10 μM) |
| Downstream primer (TK-Poly A) | 2.5 μL (10 μM) |
| dNTP | 4 μL |
| 10× buffer | 5 μL |
| TransStart Taq DNA polymerase | 1 μL |
| Deionized water | to 50 μL |

PCR reaction conditions: firstly pre-denaturation at 95° C. for 5 min; then 30 cycles of 95° C., 30 s; 60° C., 30 s; 72° C., 3 min; finally elongation at 72° C. for 10 min.

PCR reaction products are directly recovered with the OMEGA kit and quantified with Nano (GE Healthcare). One day before transfection, $2 \times 10^4$ cells in 150 μL medium were seeded into each well of 96-well plates. On the day of transfection, took 0.2 μg of each light and heavy chain, added 0.8 μL of Turbofect transfection reagent, diluted to 40 μL with DMEM medium, and incubated at room temperature for 15 min after mixing. The mixtures were slowly added dropwise to 96-well plates and then cultured in a 37° C. incubator for 48 h.

6. Screening of Antibodies with Binding Capacity by ELISA

1) One day before the experiment, microplates are coated with 100 μL of NiV-BD G at 1 μg/mL and incubated overnight at 4° C. in a humid box.

2) On the following day, plates are washed 5 times with a plate washer (BIO-TEK, 405_LS). After adding 100 μL of blocking buffer to each well, plates are incubated at 37° C. for 1 h.

3) After washed by plater-washer, plates are added 100 μL of the transfected cell culture supernatant and then incubated at 37° C. for 1 h.

4) After washed, plates are added 100 μL of HRP-labelled goat anti-human IgG (Abcam, Ab97225) at a dilution of 1:10,000, and then incubated at 37° C. for 1 h.

5) After washed, plates are added 100 μL of TMB substrate for 6 min in the dark at room temperature, followed by addition of 50 μL stop solution. Optical density at a 450-630 nm is read on a microplate reader.

Figure 3:
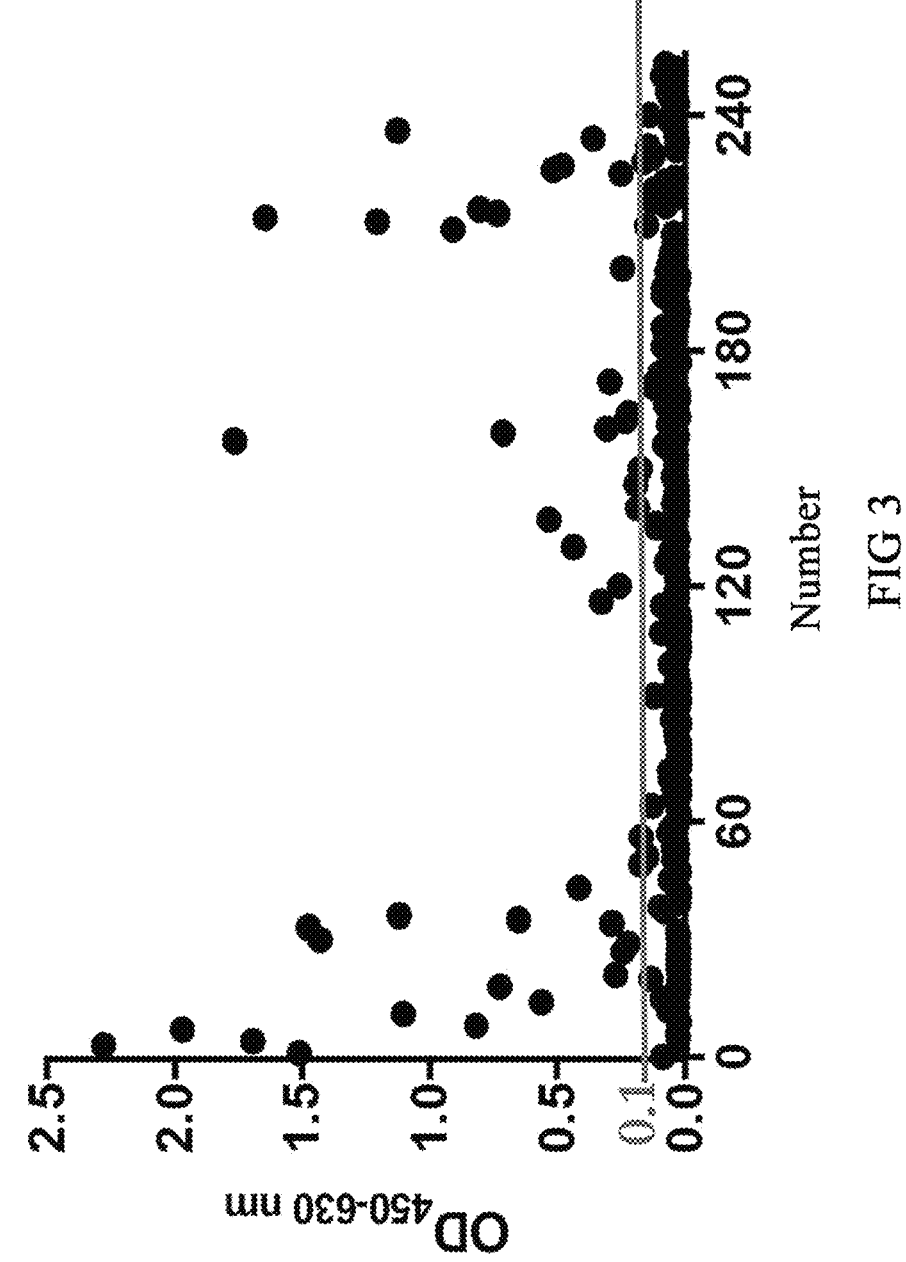
FIG. 3. Distribution of ELISA $OD_{450-630\ nm}$ values for screening of binding antibodies.

Results: Taking 0.1 as the cutoff value of optical density. Fifty-nine antibodies that can specifically bind to NiV-BDG were screened from 254 amplified positive clones. These antibodies were further expressed, purified and verified. Distribution of OD values for ELISA screening of antibodies with binding capacity is shown in FIG. 3.

7. Construction of the Expression Plasmid Construction and Preparation of the Antibody The expression plasmids are constructed and then the antibodies are preparation by expression. The method is described as follows:

1) Full-length genes of heavy chain and light chain linear expression cassettes are digested with EcoR I (NEB, R3101) and Not I (NEB, R3189), then ligated into pcDNA3.4 expression plasmids.

2) 15 μg of pcDNA3.4-H and 15 μg of pcDNA3.4-L are co-transfected into 30 mL Expi293 system (Life, A14524), and cells are cultured at 125 rpm, 5% $CO_2$ for 72 h.

3) The expression supernatant is collected by centrifugation at 3000×g for 10 min. Antibodies are purified using a rProtein A column. Antibodies are buffer-exchanged into PBS and then quantified by BCA protein quantification kit (Thermo Scientific, 23225).

Example 2. Detection of the Binding Capacity of the Antibody by ELISA

1) One day before the assay, microplates are coated with 100 μL of NiV-BD/MY G or HeV G (NiV-BD G, Genbank: AY988601.1; NiV-MY G, Genbank: FN869553.1; HeV G, Genbank: NC_001906.3) at 1 μg/mL and incubated overnight at 4° C.

2) On the following day, after washing 5 times by a plate washer, adding 100 μL of blocking buffer to each well, plates are incubated at room temperature for 1 h.

3) Wash plates. Add 150 μL of antibodies at a concentration of 20 μg/mL to the first well, and add 100 μL of dilution solution to the remaining wells. Transfer 50 μL from the first well to the second well, and so on, dilute at a gradient of 1:3, with a final volume of 100 μL per well. Incubate plates for 1 h at room temperature.

4) Wash plates. Add 100 μL of HRP-labelled goat anti-human IgG (Abcam, Ab97225) at a dilution of 1:10,000 into each well, and then incubated at room temperature for 1 h.

5) Wash plates. Plates are added 100 μL of TMB substrate for 6 min in the dark at room temperature, followed by addition of 50 μL stop solution.

6) Read optical density at a 450-630 nm on a microplate reader.

Figure 4:
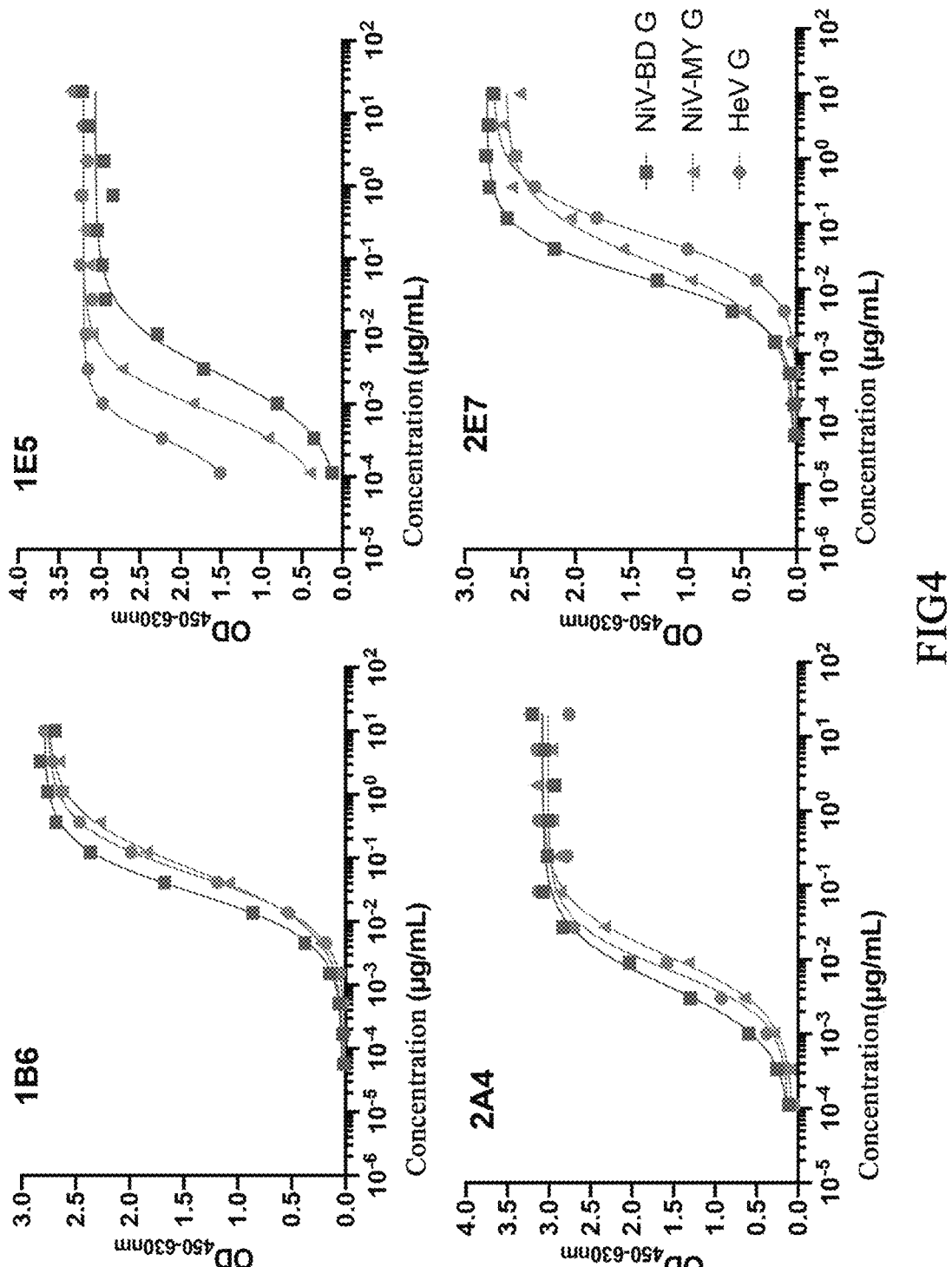
FIG. 4. The curves of antibody binding with antigen in ELISA detection.

As shown in FIG. 4, antibodies have good binding capacity to the protein G of NiV-BD, NiV-MY and HeV. Among them, the half effective concentration ($EC_{50}$) values of antibody 1B6 are 28.43 ng/mL, 63.92 ng/mL and 52.93 ng/mL, respectively; the $EC_{50}$ values of antibody 1E5 are 2.6 ng/ml, 0.85 ng/ml and 0.34 ng/ml, respectively; the $EC_{50}$ values of antibody 2A4 are 4.50 ng/ml, 11.23 ng/ml and 7.37 ng/mL, respectively; the $EC_{50}$ values of antibody 2E7 are 15.4 ng/ml, 26.69 ng/ml and 70.05 ng/ml, respectively.

The sequences of the above-mentioned four antibodies are sequenced. The nucleotide sequences of the heavy chain variable region of 1B6 is shown as SEQ ID NO:2; the nucleotide sequences of the light chain variable region of 1B6 is shown as SEQ ID NO:4; the amino acid sequences of the heavy chain variable regions of 1B6 is shown as SEQ ID NO:1; the amino acid sequences of the light chain variable regions of 1B6 is shown as SEQ ID NO:3; further analysis on the amino acid sequences of the heavy chain and the light chain variable region shows, the amino acid sequences of the CDR1, CDR2 and CDR3 region of the heavy chain variable region are respectively shown as 26-33, 51-58, and 97-116 of SEQ ID NO:1, the amino acid sequences of CDR1, CDR2 and CDR3 regions of the light chain variable region are respectively shown as 27-36, 54-56, and 93-100 of SEQ ID NO:3.

The nucleotide sequences of the heavy chain variable region of 1E5 is shown as SEQ ID NO:6; the nucleotide sequences of the light chain variable region of 1E5 is shown as SEQ ID NO:8; the amino acid sequences of the heavy chain variable regions of 1E5 is shown as SEQ ID NO:5; the amino acid sequences of the light chain variable regions of 1E5 is shown as SEQ ID NO:7; further analysis on the amino acid sequences of the heavy chain and the light chain variable region shows, the amino acid sequences of the CDR1, CDR2 and CDR3 of the heavy chain variable region are respectively shown as 26-33, 51-58, and 97-117 of SEQ ID NO:5, the amino acid sequences of CDR1, CDR2 and CDR3 regions of the light chain variable region are respectively shown as 27-32, 50-52, and 89-97 of SEQ ID NO:7.

The nucleotide sequences of the heavy chain variable region of 2A4 is shown as SEQ ID NO:10; the nucleotide sequences of the light chain variable region of 2A4 is shown as SEQ ID NO: 12; the amino acid sequences of the heavy chain variable regions of 2A4 is shown as SEQ ID NO:9; the amino acid sequences of the light chain variable regions of 2A4 is shown as SEQ ID NO:11; further analysis on the amino acid sequences of the heavy chain and the light chain variable region shows, the amino acid sequences of the CDR1, CDR2 and CDR3 of the heavy chain variable region are respectively shown as 26-33, 51-58, and 97-115 of SEQ ID NO:9, the amino acid sequences of CDR1, CDR2 and CDR3 regions of the light chain variable region are respectively shown as 27-32, 50-52, and 89-97 of SEQ ID NO:11.

The nucleotide sequences of the heavy chain variable region of 2E7 is shown as SEQ ID NO:14; the nucleotide sequences of the light chain variable region of 2E7 is shown as SEQ ID NO: 16; the amino acid sequences of the heavy chain variable regions of 2E7 is shown as SEQ ID NO: 13; the amino acid sequences of the light chain variable regions of 2E7 is shown as SEQ ID NO:15; further analysis on the amino acid sequences of the heavy chain and the light chain variable region shows, the amino acid sequences of CDR1, CDR2 and CDR3 region of the heavy chain variable region are respectively shown as 26-33, 51-58, and 97-109 of SEQ ID NO:13, the amino acid sequences of CDR1, CDR2 and CDR3 regions of the light chain variable region are respectively shown as 27-37, 51-53, and 90-100 of SEQ ID NO:15.

Four monoclonal antibodies have the same human heavy chain and light chain constant regions. The sequence of the polynucleotide encoding the heavy chain constant region is shown as SEQ ID NO:18, and the sequence of the polynucleotide encoding the light chain constant region is shown as SEQ ID NO:20 or SEQ ID NO:22, the amino acid sequence of the heavy chain constant region is shown as SEQ ID NO: 17, and the amino acid sequence of the light chain constant region is shown as SEQ ID NO: 19 or SEQ ID NO:21.

Example 3. Affinity Determination of Antibody 1E5

Figure 5:
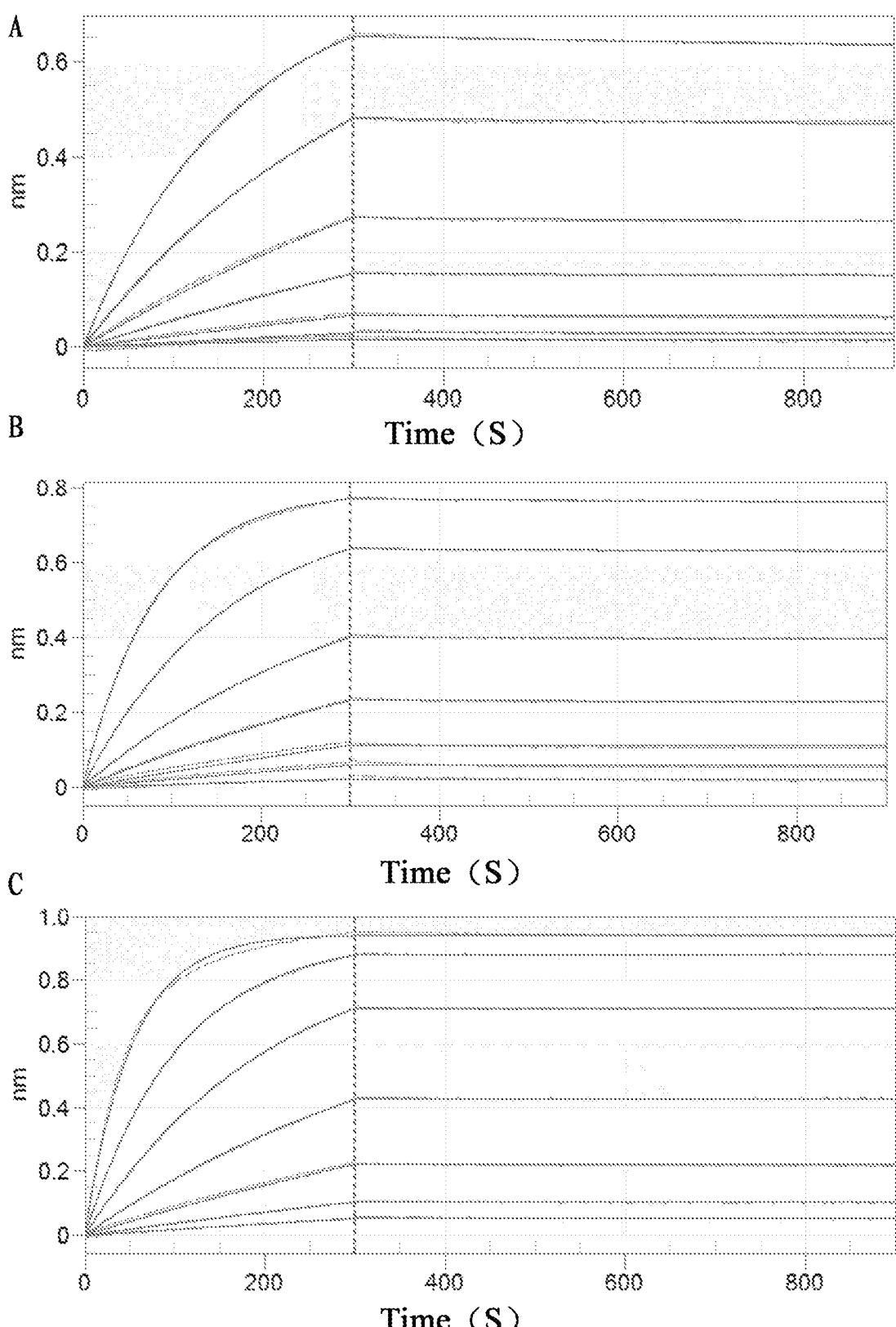
FIG. 5. Affinity determination of 1E5 to Henipavirus G protein.
Figure 6:
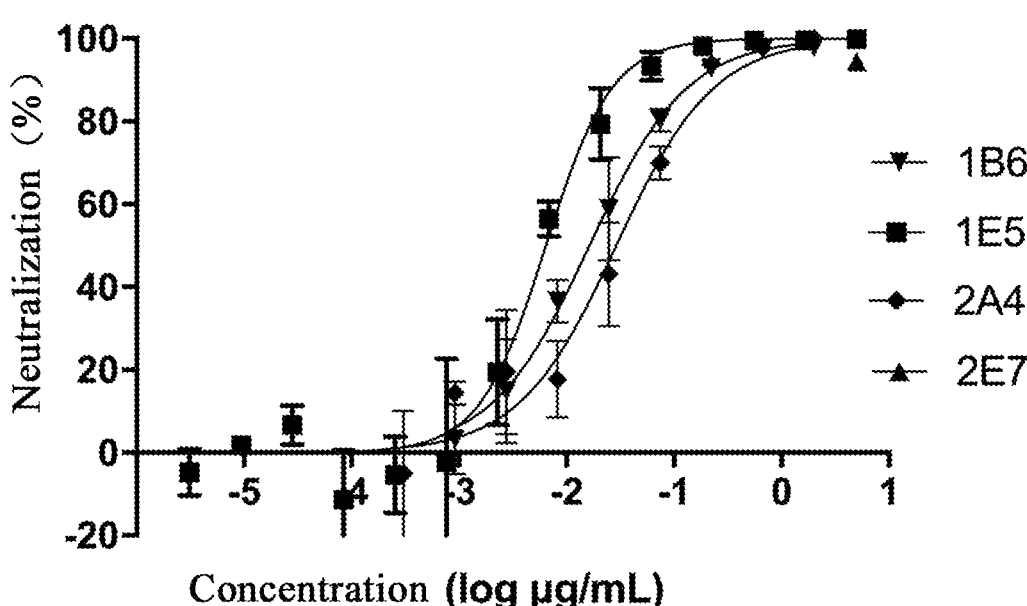
FIG. 6. The neutralization curves of mAbs against HeV pseudovirus.
Figure 7:
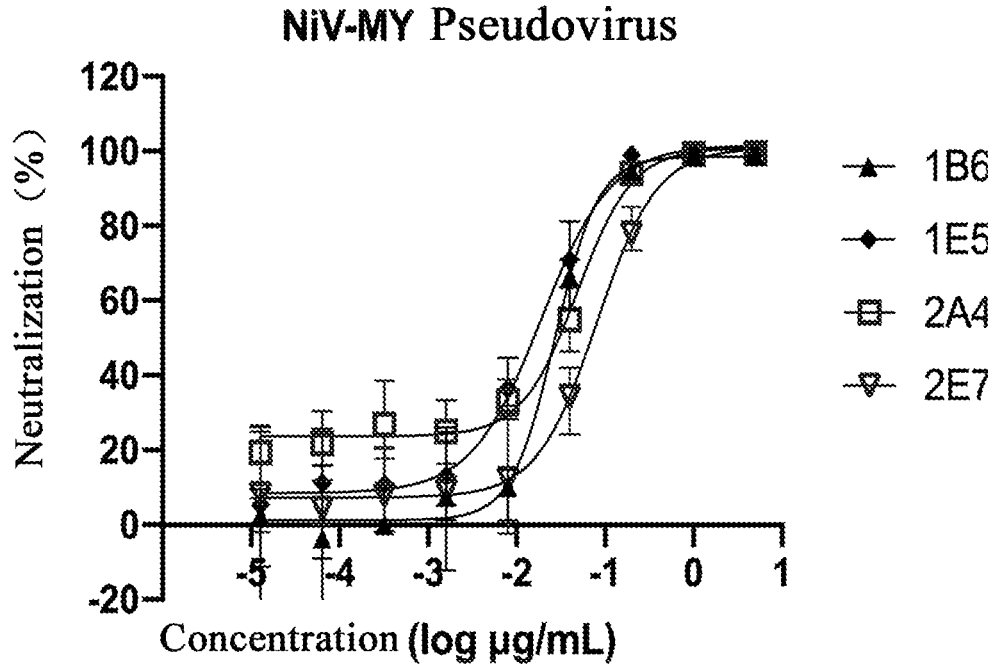
FIG. 7. The neutralization curves of mAbs against NiV-MY pseudovirus.
Figure 8:
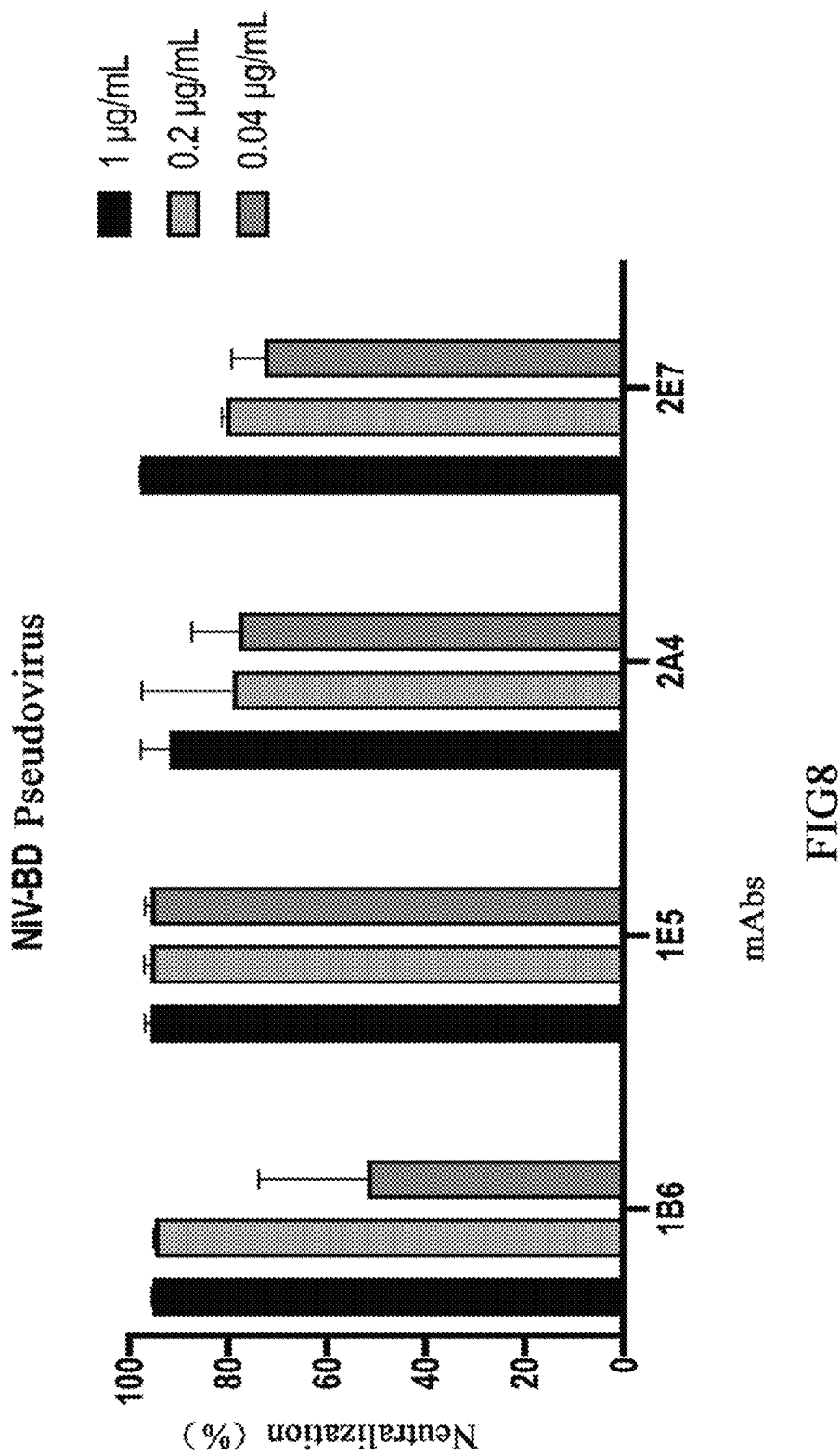
FIG. 8. The neutralization activity of mAbs against NiV-BD pseudovirus.

1) Dilute 1E5 to concentrations of 100 nM, 50 nM, 25 nM, 12.5 nM, 6.25 nM, 3.13 nM, and 1.56 nM, respectively.
2) Prepare the Octet RED instrument (fortéBIO, Pall Corp, USA) and set the kinetic detection method in the companion software Data Analysis Software v9.0. The method includes 5 steps: baseline, loading, baseline, association and dissociation, and the duration of each step is set to 100 s, 180 s, 60 s, 300 s and 600 s respectively.
3) Place the antibody, antigen, and PBS buffer, and then start the assay. After the experiment, the software DataAnalysis was used for data processing, and the equilibrium dissociation constant KD value and the binding dissociation curve of 1E5 with Henipavirus G proteins are fitted and calculated. As shown in FIG. 5, A, B and C are the curves of 1E5 binding and dissociation with HeV G, NiV-BD G, and NiV-MY G, respectively. The calculation results of the KD value are shown in the table below.

TABLE 9

Affinity of 1E5 to Henipavirus G protein

| | Antigen | | |
| --- | --- | --- | --- |
| | NiV-BD G | NiV-MY G | HeV G |
| KD | 0.171 nM | <0.001 nM | 0.785 nM |

1E5 has high affinity to all three G proteins, and the affinity constant KD is less than 1 nM. The highest affinity is to NiV-MY G and the lowest is to HeV G.

Example 4. Pseudovirus Neutralization Assay to Evaluate the Neutralizing Capacity of the Antibodies Package of human immunodeficiency virus (HIV)-backboneNiV-BD, NiV-MY and HeVpseudoviruses to evaluate the neutralizing capacity of monoclonal antibodies in vitro (Dimple Khetawat, C.C.B., A functional Henipavirus envelope glycoprotein pseudotyped lentivirus assay system. Virology Journal 2010. 7(312)). Method is as below:

1) Dilute antibodies with DMEM medium, add 75 μL of antibody at 5 μg/mL to the first well of 96-well culture plates, and add 50 μL of DMEM medium to the remaining wells.
2) Transfer 25 μL of liquid from the first well into the second well, mix well, and so on, dilute at a ratio of 1:3, and the final volume of each well is 50 μL. Add 50 μL pseudovirus to each well and incubate at 37° C. for 1 h.
3) Count 293T cells and seed 100 μL cells at a density of $2\times10^5$ cells/mL to each well. Place the culture plate in a 37° C. incubator for 36-48 h.
4) Take out plates. Carefully remove the medium. Add 100 μL of cell lysate to each well and shake at 400 rpm for 15 min on a shaker. Centrifuge at 3000 rpm for 10 min at room temperature. After mixing the lyophilized detection substrate and buffer of the luciferase detection system (Promega, E1501), then fill them in the GLOMAX 96 Microplate Luminometer (Promega) detection loops. Transfer 20 μL of the lysis supernatant and read the fluorescence value. Calculate the protection rate of the antibody on the cells.

The results are shown in FIG. 6, FIG. 7 and FIG. 8, 1B6, 1E5, 2A4 and 2E7 can effectively neutralize three pseudoviruses of HIV-NiV-BD, -NiV-MY, and -HeV in vitro. Among them, the neutralizing capacity of 1B6, 1E5 and 2A4 increased with the increase of its concentration, and nearly 100% neutralization against the three pseudotyped Henipaviruses could be achieved at a concentration of 1 μg/mL. As for HeVpseudovirus, the half inhibiting concentration ($IC_{50}$) values of 1B6, 1E5 and 2A4 are 16.31 ng/mL, 5.74 ng/mL and 28.96 ng/mL, respectively, and 2E7 could be nearly 100% neutralized at 5 μg/mL. As for NiV-BD and NiV-MY pseudovirus, all four antibodies have good neutralizing activity, and the $IC_{50}$ values against NiV-MY pseudovirus are 27.15 ng/mL, 19.03 ng/mL, 48.60 ng/mL and 80.79 ng/ml, respectively. These results indicate that the four monoclonal antibodies 1B6, 1E5, 2A4 and 2E7 have broad-spectrum neutralizing capacity, and can simultaneously neutralize Nipah virus and Hendra virus of the Henipavirus genus.

Example 5. Competition Experiment

The capacity of monoclonal antibody inhibiting the binding of Henipavirus G protein with the receptor was evaluated through Luminex microsphere competitive inhibition assay. The method is described as follows:

1) Add 10 μL of 10 μg monoclonal antibody to the first well, and then dilute it by two times successively.
2) Add 1.25 ng of receptor ephrin-B2 or ephrin-B3 to each well in a volume of 10 μL. Add 10 μL of prepared microspheres (containing 1500 NiV-BD/MY G-coupled microspheres respectively) to each well, and incubate on a shaker for 60 min.
3) Add 10 μL of SAPE (concentration of 12 μg/mL) to each well and incubate on a shaker for 30 min.
4) Wash 3 times with 100 μL assay buffer and read on Luminex MAGPIX instrument.

Figure 9:
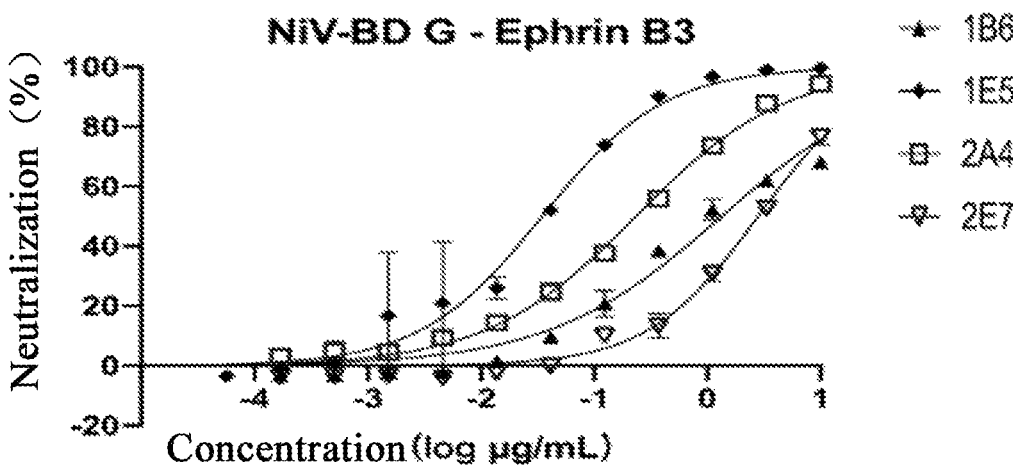
FIG. 9. Competitive inhibition on the binding of Henipavirus G protein with receptor ephrin-B3 by mAbs.
Figure 9:
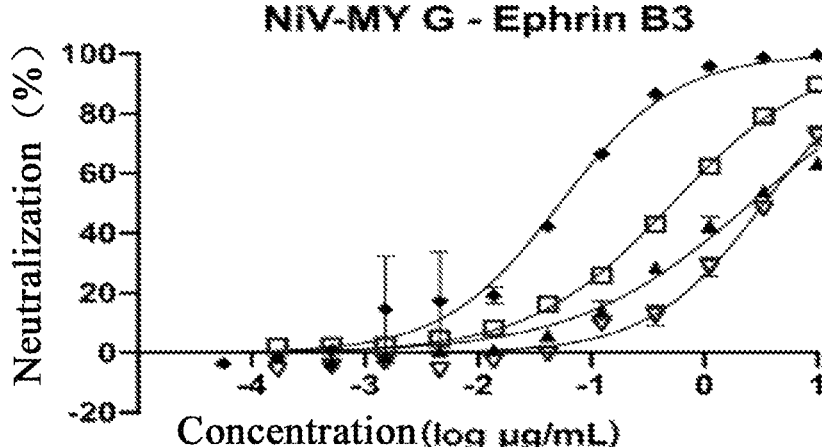
Figure 9:
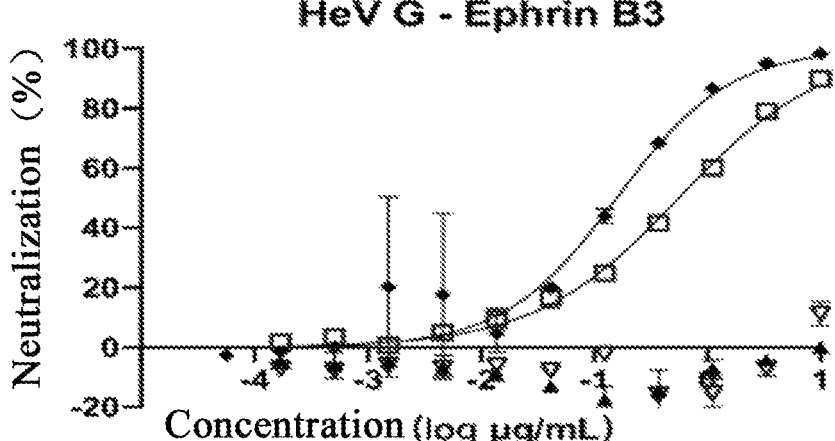
Figure 10:
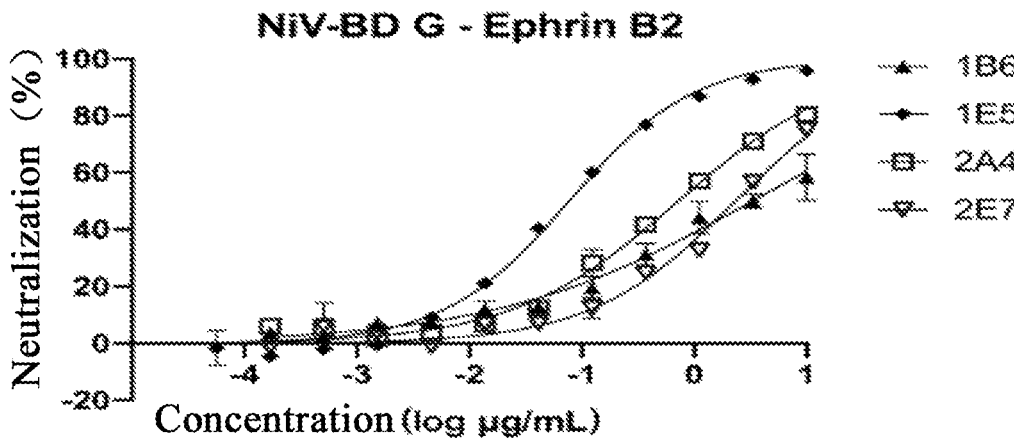
FIG. 10. Competitive inhibition on the binding of Henipavirus G protein with receptor ephrin-B2 by mAbs.
Figure 10:
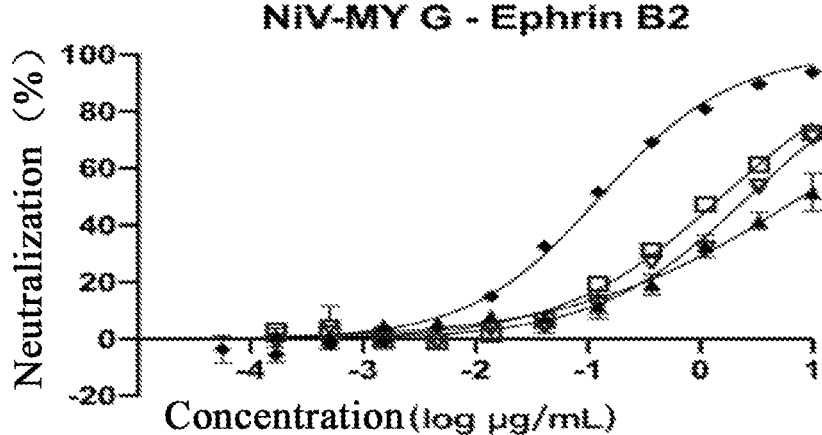
Figure 10:
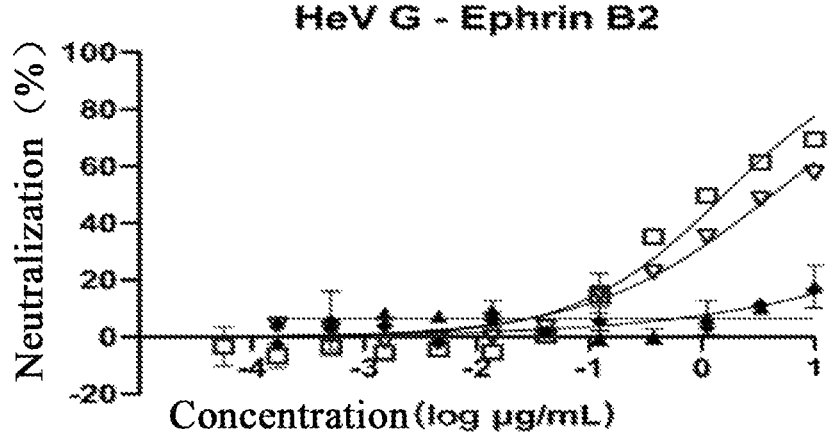

The curves of antibodies competitively inhibiting of the binding of Henipavirus G protein with receptor ephrin-B2/B3 are shown in FIGS. 9 and 10. The results show that 1E5 and 2A4 can effectively inhibit the binding of Henipavirus G protein with receptor ephrin-B2/B3 binding; 1B6 and 2E7 can effectively inhibit the binding of Nipah virus G protein with the receptor ephrin-B2/B3, but fail to inhibit Hendra virus G protein binding with the receptor. It is suggested that antibodies 1E5 and 2A4 are likely to play a neutralizing role by inhibiting the binding of Henipavirus G protein with receptor ephrin-B2/B3, while 1B6 and 2E7 may have other neutralizing mechanisms against Hendra virus.

Example 6. Escape Variant Neutralization Experiments

Figure 11:
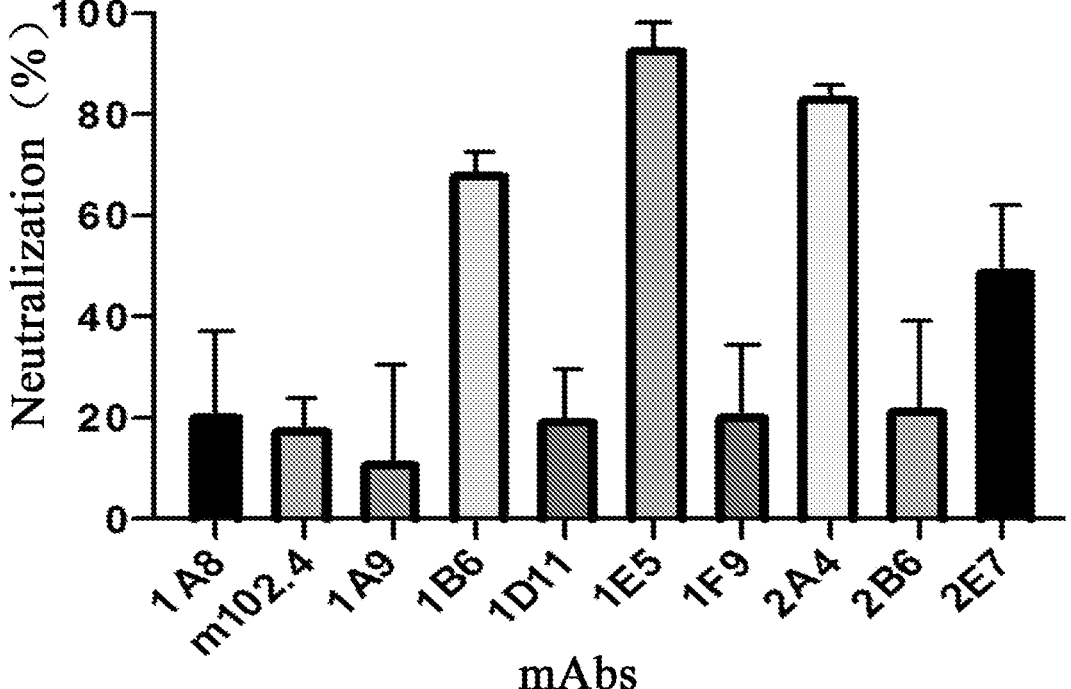
FIG. 11. The neutralization activity of mAbs against HeV-G-D582N variant pseudovirus.

The reported antibody m102.4-escape variant HeV G-D582N (synthesized by Sangon Biotech, Genbank: NC_001906.3. The exceptionally large genome of Hendra virus: support for creation of a new genus within the family Paramyxoviridae. J. Virol. 74 (21), 9972-9979 (2000)) pseudovirus was used to perform neutralization experiments. The amino acid D at position 582 was mutated to N during synthesis, and the pseudovirus was packaged according to Example 4. The results are shown in FIG. 11. When the antibody concentration was 1 μg/mL, mAbs 1B6, 1E5 and 2A4 had over 60% inhibition activity against D582N pseudovirus, 2E7 had 50% neutralization activity, and the remaining antibodies were all below 20%. This indicates that the antibodies disclosed in the invention can be used to neutralize the Henipavirus mutant strain escaping from 102.4, which have different binding epitopes from that of m102.4.

INDUSTRIAL APPLICABILITY

The invention provides a series of anti-Henipavirus monoclonal antibodies with broad-spectrum neutralizing capacity and their application in the preparation of medicines. The monoclonal antibodies are easy to be industrially produced and have industrial practicability.

---

The invention claimed is:

1. A monoclonal antibody against Henipavirus glycoprotein G, wherein the amino acid sequence of the CDR1, CDR2, and CDR3, of the heavy chain variable region of the said antibody and the amino acid sequence of the CDR1, CDR2, and CDR3 of the light chain variable region of the said antibody are respectively shown as the following sequence combinations:

26-33, 51-58, 97-116 of SEQ ID NO:1 and 27-36, 54-56, 93-100 of SEQ ID NO:3, or 26-33, 51-58, 97-117 of SEQ ID NO:5 and 27-32, 50-52, 89-97 of SEQ ID NO:7, or 26-33, 51-58, 97-115 of SEQ ID NO:9 and 27-32, 50-52, 89-97 of SEQ ID NO: 11, or 26-33, 51-58, 97-109 of SEQ ID NO:13 and 27-37, 51-53, 90-100 of SEQ ID NO:15.

2. The monoclonal antibody of claim 1, wherein the amino acid sequence of the heavy chain variable region of the said antibody and the amino acid sequence of the light chain variable region of the said antibody are respectively shown as the following sequence combinations:

SEQ ID NO:1 and SEQ ID NO:3, or
SEQ ID NO:5 and SEQ ID NO:7, or
SEQ ID NO:9 and SEQ ID NO:11, or
SEQ ID NO:13 and SEQ ID NO:15.

3. The monoclonal antibody of claim 2, wherein the antibody comprises a heavy chain constant region and a light chain constant region, and wherein the amino acid sequence of the heavy chain constant region of the said antibody is shown as SEQ ID NO:17, and the amino acid sequence of the light chain constant region of the said antibody is shown as SEQ ID NO: 19 or SEQ ID NO:21.

4. An isolated nucleic acid encoding the variable region of the heavy chain and light chain of the monoclonal antibody of claim 1, wherein the sequence of the isolated nucleic acid encoding the variable region of the heavy chain and the sequence of the isolated nucleic acid encoding the variable region of the light chain of the monoclonal antibody are respectively shown as the following sequence combinations:

SEQ ID NO:2 and SEQ ID NO:4, or
SEQ ID NO:6 and SEQ ID NO:8, or
SEQ ID NO:10 and SEQ ID NO:12, or
SEQ ID NO: 14 and SEQ ID NO: 16.

5. The isolated nucleic acid of claim 4, wherein the sequence of the isolated nucleic acid encoding a heavy chain constant region is shown as SEQ ID NO:18, and the sequence of the isolated nucleic acid encoding a light chain constant region is shown as SEQ ID NO:20 or SEQ ID NO:22.

6. A functional element expressing the isolated nucleic acid of claim 5, wherein the functional element is a linear expression cassette.

7. A host cell comprising the functional element of claim 6.

8. The host cell of claim 7, wherein the cell is an Expi 293F cell or a CHO-S cell.

9. A method of preparing the monoclonal antibody of claim 1 as a therapeutic drug for treating Henipavirus disease.

* * * * *

SEQUENCE LISTING

<160> NUMBER OF SEQ ID NOS: 22

<210> SEQ ID NO 1
<211> LENGTH: 127
<212> TYPE: PRT
<213> ORGANISM: Macaca mulatta

<400> SEQUENCE: 1

```
Val Gln Leu Gln Glu Ser Gly Pro Gly Pro Val Lys Pro Ser Glu Thr
1               5                   10                  15

Leu Ser Leu Thr Cys Thr Val Ser Gly Gly Ser Met Ser Arg Gly Tyr
            20                  25                  30

Asp Trp Asn Trp Ile Arg Gln Pro Pro Gly Lys Gly Leu Glu Trp Ile
        35                  40                  45

Gly Tyr Ile Gly Asp Asp Gly Gly Arg Ser Asn Tyr Asn Pro Ser Leu
    50                  55                  60

Lys Ser Arg Val Thr Ile Ser Lys Asp Ser Ser Lys Asn Gln Phe Ser
65                  70                  75                  80

Leu Lys Leu Gly Ser Val Ser Ala Ala Asp Thr Ala Val Tyr Tyr Cys
                85                  90                  95

Ala Arg Ala Leu Arg Ala Ile Trp Tyr Asn Ser Gly Trp Phe Tyr Asn
            100                 105                 110

Ser Leu Asp Val Trp Gly Arg Gly Val Leu Val Thr Val Ser Ser
            115                 120                 125
```

<210> SEQ ID NO 2
<211> LENGTH: 382
<212> TYPE: DNA
<213> ORGANISM: Macaca mulatta

<400> SEQUENCE: 2

```
gtgcagctgc aggagtcggg cccagggccg gtgaagcctt cggagaccct gtccctcacc        60
tgcactgtct ctggtggctc catgagcaga ggttatgact ggaactggat ccgccagccc       120
ccagggaaag ggctggagtg gattggttat atcggtgatg atggtggcag atccaactac       180
aacccctccc tcaagagtcg agtcaccatt tcaaaagact cgtccaagaa ccagttctcc       240
ctgaagctgg gctctgtgag cgccgcggac accgccgtgt attactgtgc gagagcgctg       300
agggccatct ggtataacag cggctggttc tacaattcat ggatgtctg gggccgggga        360 gttctggtca ccgtctcctc ag                                                382
```

<210> SEQ ID NO 3
<211> LENGTH: 110
<212> TYPE: PRT
<213> ORGANISM: Macaca mulatta

<400> SEQUENCE: 3

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Gly Val Ser Val Phe
                20                  25                  30

Gly Arg Asp Leu Ile His Trp Tyr Gln Gln Lys Pro Gly Gln Pro Pro
            35                  40                  45

Lys Leu Leu Ile Tyr Gln Thr Ser Asn Arg Asp Thr Gly Val Pro Ala
        50                  55                  60

Arg Phe Ser Gly Ser Gly Ser Gly Thr Asp Phe Thr Leu Thr Ile Asn
65                  70                  75                  80

Pro Val Glu Ala Asp Asp Ala Ala Asp Tyr Tyr Cys Leu Gln Ser Lys
                85                  90                  95

Asn Ser Tyr Ser Phe Gly Gln Gly Thr Lys Val Glu Ile Lys
            100                 105                 110

<210> SEQ ID NO 4
<211> LENGTH: 331
<212> TYPE: DNA
<213> ORGANISM: Macaca mulatta

<400> SEQUENCE: 4
gacattgtgc tgacccagtc tccagcctct ttggccgtgt ctccagggca gagggccacc      60
atcacctgca gagccagtga gggtgtcagt gtctttggaa gagacctcat tcactggtat     120
caacagaaac caggacaacc tcctaaactc ctgatttatc aaacatccaa tagagacact     180
ggggtcccag ccaggttcag cggcagtggg tctgggaccg atttcaccct cacaattaat     240
cctgtggaag ctgacgatgc tgcagattat tactgtctgc agagtaagaa ttcgtacagt     300
tttggccagg ggaccaaagt ggagatcaaa c                                    331

<210> SEQ ID NO 5
<211> LENGTH: 128
<212> TYPE: PRT
<213> ORGANISM: Macaca mulatta

<400> SEQUENCE: 5

Val Gln Leu Gln Glu Ser Gly Pro Gly Val Val Lys Pro Ser Glu Thr
1               5                   10                  15

Leu Ser Leu Thr Cys Ala Val Ser Gly Gly Ser Ile Ser Asp Thr Tyr
                20                  25                  30

Arg Trp Ser Trp Ile Arg Gln Pro Pro Gly Lys Gly Leu Glu Trp Ile
            35                  40                  45

Gly Tyr Ile Tyr Gly Ser Ala Thr Ser Thr Tyr Tyr Asn Pro Ser Leu
        50                  55                  60

Ser Ser Arg Val Thr Ile Ser Lys Asp Met Ser Lys Asn Gln Phe Ser
65                  70                  75                  80

Leu Asn Leu Asn Ser Val Thr Ala Ala Asp Thr Ala Val Tyr Tyr Cys
                85                  90                  95

Ala Arg Asp Tyr Gln Tyr Tyr Tyr Ser Gly Ser Tyr Pro Thr Pro His
            100                 105                 110

Asn Trp Phe Asp Val Trp Gly Pro Gly Val Leu Val Thr Val Ser Ser
    115                 120                 125

<210> SEQ ID NO 6
<211> LENGTH: 384
<212> TYPE: DNA
<213> ORGANISM: Macaca mulatta

<400> SEQUENCE: 6
gtgcagctgc aggagtcggg cccaggagta gtgaagcctt cggagaccct gtccctcacc      60
tgcgctgtct ctggtggctc catcagcgat acttatcggt ggagctggat ccgccagccc     120
ccagggaagg gactggagtg gattgggtac atctatggta gtgctacgag cacctactac     180
aacccctccc tcagcagtcg agtcaccatt tcaaaagaca cgtccaagaa ccagttctcc     240
ttgaacctga actctgtgac cgccgcggac acggccgtgt attactgtgc gagagattac     300
caatattact atagtggttc ttatccaacc ccccacaact ggttcgatgt ctggggcccg     360
ggagtcctgg tcaccgtctc ctca                                            384

<210> SEQ ID NO 7
<211> LENGTH: 107
<212> TYPE: PRT
<213> ORGANISM: Macaca mulatta

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ile Asp Tyr
            20                  25                  30

Leu Ser Trp Tyr Gln Gln Lys Pro Gly Lys Ala Pro Lys Leu Leu Ile
        35                  40                  45

Ser Thr Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Ser Cys Leu Gln Gly Tyr Thr Thr Pro Tyr
                85                  90                  95

Thr Phe Gly Gln Gly Thr Lys Val Glu Ile Lys
            100                 105

<210> SEQ ID NO 8
<211> LENGTH: 321
<212> TYPE: DNA
<213> ORGANISM: Macaca mulatta

<400> SEQUENCE: 8
gacatccaga tgacccagtc tccatcttcc ctgtctgcat cggtaggaga cagagtcacc      60
atcacttgca gggcaagtca gggcattatc gattatttaa gttggtatca gcagaaacca     120
ggaaaagccc ctaagctcct gatctctact gcatccaatt tggaaagcgg ggtcccatca     180
aggttcagcg gcagtggatc tgggacagaa ttcactctca ccatcagcag cctgcagcct     240
gaagattttg caacttattc ctgtctacag ggttatacta ccccgtacac ttttggccag     300
gggaccaaag tggagatcaa a                                                321

<210> SEQ ID NO 9
<211> LENGTH: 126
<212> TYPE: PRT
<213> ORGANISM: Macaca mulatta -continued

<400> SEQUENCE: 9

```
Gln Val Gln Leu Gln Glu Ser Gly Pro Gly Leu Val Lys Pro Ser Glu
1               5                   10                  15

Thr Leu Ser Leu Thr Cys Pro Val Ser Gly Ala Ser Ile Ser Ser His
            20                  25                  30

Trp Trp Thr Trp Ile Arg Gln Pro Pro Gly Lys Gly Leu Glu Trp Ile
            35                  40                  45

Gly Glu Ile His Gly Asn Ser Gly Ser Thr Asn Tyr Asn Pro Ser Leu
        50                  55                  60

Lys Ser Arg Val Thr Ile Ser Lys Asp Ala Ser Lys Asn His Phe Ser
65                  70                  75                  80

Leu Lys Leu Ser Ser Val Thr Ala Ala Asp Thr Ala Val Tyr Tyr Cys
                85                  90                  95

Ala Arg Asp Gly His Leu Gly Ile Leu Val Val Phe Ala Thr Ser Arg
            100                 105                 110

Phe Asp Val Trp Gly Pro Gly Val Leu Val Thr Val Ser Ser
            115                 120                 125
```

<210> SEQ ID NO 10
<211> LENGTH: 379
<212> TYPE: DNA
<213> ORGANISM: Macaca mulatta

<400> SEQUENCE: 10

```
caggtgcagc tgcaggagtc gggcccagga ctggtgaagc cttcggagac cctgtccctc        60
acctgccctg tctctggtgc ctccatcagt agtcactggt ggacctggat ccgccagccc       120
ccagggaagg gactggagtg gattggggag atccatggta atagtgggag caccaactac       180
aacccctccc tcaagagtcg agtcaccatt tcaaaagacg cgtccaagaa ccacttctcc       240
ctgaagctga gctctgtgac cgccgcggac acggccgtgt attattgtgc gagagatggg       300
caccttggta ttctggtggt atttgcgact agccggttcg atgtctgggg cccgggagtc       360
ctggtcaccg tctcctcag                                                    379
```

<210> SEQ ID NO 11
<211> LENGTH: 107
<212> TYPE: PRT
<213> ORGANISM: Macaca mulatta

<400> SEQUENCE: 11

```
Asp Ile Gln Met Thr Gln Ser Pro Ser Ser Leu Ser Ala Ser Val Gly
1               5                   10                  15

Asp Thr Val Thr Ile Thr Cys Gln Ala Ser Gln Gly Ile Ala Asn Asn
            20                  25                  30

Leu Asn Trp Tyr Gln Gln Lys Pro Gly Lys Ala Pro Lys Leu Leu Ile
            35                  40                  45

Tyr Arg Ala Ser Ser Leu Gln Ser Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Tyr Thr Tyr Pro Arg
                85                  90                  95

Thr Phe Gly Gln Gly Thr Lys Val Glu Ile Lys
            100                 105
```

```
<210> SEQ ID NO 12
<211> LENGTH: 322
<212> TYPE: DNA
<213> ORGANISM: Macaca mulatta

<400> SEQUENCE: 12
gacatccaga tgacgcagtc tccatcctcc ctgtccgcat ctgtaggaga cacggtcacc      60
atcacttgcc aggcgagtca aggcattgcc aataatttaa attggtatca gcagaaacca     120
gggaaagccc ctaaactcct gatctatagg gcatccagtt tgcaaagtgg gattccctct     180
cggttcagtg gcagtggatc tgggacggat tacactctca ccatcagcag cctgcagcct     240
gaagattttg ccacttatta ctgtcaacag ggttatactt accctcggac gttcggccaa     300
gggaccaagg tggaaatcaa ac                                              322

<210> SEQ ID NO 13
<211> LENGTH: 120
<212> TYPE: PRT
<213> ORGANISM: Macaca mulatta

<400> SEQUENCE: 13

Val Gln Leu Gln Glu Ser Gly Pro Gly Leu Val Lys Pro Ser Glu Thr
1               5                   10                  15

Leu Ser Leu Thr Cys Ser Val Ser Gly Gly Ser Ile Ser Ile Ser Asn
            20                  25                  30

Trp Trp Ser Trp Ile Arg Gln Ser Pro Gly Lys Gly Leu Glu Trp Ile
        35                  40                  45

Gly Tyr Ile Tyr Gly Ser Ser Gly Ser Thr Leu Tyr Asn Pro Ser Leu
    50                  55                  60

Lys Ser Arg Val Ser Ile Ser Thr Asp Thr Ser Lys Asn Gln Phe Ser
65                  70                  75                  80

Leu Lys Leu Arg Ser Val Thr Ala Ala Asp Thr Ala Val Tyr Tyr Cys
                85                  90                  95

Ala Ser Pro Ser Ile Ala Ala Thr Gly Asp Phe Asp Tyr Trp Gly Gln
            100                 105                 110

Gly Val Leu Val Thr Val Ser Ser
        115                 120

<210> SEQ ID NO 14
<211> LENGTH: 361
<212> TYPE: DNA
<213> ORGANISM: Macaca mulatta

<400> SEQUENCE: 14
gtgcagctgc aggagtcggg cccaggactg gtgaagcctt cggagaccct gtccctcacc      60
tgctctgtct ctggtggctc catcagcatt agtaactggt ggagctggat ccgccagtcc     120
ccagggaagg gctggagtg gattggatat atctatggta gtagtgggag caccctctac     180
aacccctccc tcaagagtcg agtctccatt tcaacagaca cgtccaagaa ccagtttttcc     240 ctgaagctga ggtctgtgac cgccgcggac accgccgtgt attactgtgc gagtccaagt     300
atagcagcga ctggggactt tgactactgg ggccagggag tcctggtcac cgtctcctca     360
g                                                                     361

<210> SEQ ID NO 15
<211> LENGTH: 110
<212> TYPE: PRT
<213> ORGANISM: Macaca mulatta
```

-continued

```
<400> SEQUENCE: 15

Gln Ser Val Leu Thr Gln Pro Pro Ser Ala Ser Gly Ala Pro Gly Gln
1               5                   10                  15

Ser Val Thr Ile Ser Cys Ser Gly Ser Ser Asn Ile Gly Gly Asn
            20                  25                  30

Asn Val Tyr Trp Tyr Gln Gln Leu Pro Gly Thr Ala Pro Lys Leu Leu
        35                  40                  45

Ile Tyr Ser Ser Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Arg
65                  70                  75                  80

Ser Glu Asp Glu Ala Asp Tyr Phe Cys Ala Val Trp Asp Asp Ser Leu
                85                  90                  95

Gly Ser Pro Phe Phe Gly Gly Gly Thr Arg Leu Thr Val Leu
                100                 105                 110

<210> SEQ ID NO 16
<211> LENGTH: 331
<212> TYPE: DNA
<213> ORGANISM: Macaca mulatta

<400> SEQUENCE: 16
cagtctgtac tgactcagcc accctcagcg tctggggctc ccgggcagag tgtcaccatc      60
tcttgctctg gaagcagctc caacattgga ggtaataatg tatattggta ccaacagttg     120
ccaggaacgg cccccaaact cctcatctat tctagtaatc agcgaccctc aggagtccct     180
gaccgattct ctggctccaa gtctggcacc tcagcctccc tggccatcac tggtctccgg     240
tctgaggatg aggctgatta tttctgtgca gtttgggatg acagcctggg cagtccgttt     300
ttcggaggag ggacccggct gaccgtccta g                                    331

<210> SEQ ID NO 17
<211> LENGTH: 330
<212> TYPE: PRT
<213> ORGANISM: Homo sapiens

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

-continued

```
145              150              155              160
Tyr Val Asp Gly Val Glu Val His Asn Ala Lys Thr Lys Pro Arg Glu
                165              170              175
Glu Gln Tyr Asn Ser Thr Tyr Arg Val Val Ser Val Leu Thr Val Leu
                180              185              190
His Gln Asp Trp Leu Asn Gly Lys Glu Tyr Lys Cys Lys Val Ser Asn
                195              200              205
Lys Ala Leu Pro Ala Pro Ile Glu Lys Thr Ile Ser Lys Ala Lys Gly
    210              215              220
Gln Pro Arg Glu Pro Gln Val Tyr Thr Leu Pro Pro Ser Arg Asp Glu
225              230              235              240
Leu Thr Lys Asn Gln Val Ser Leu Thr Cys Leu Val Lys Gly Phe Tyr
                245              250              255
Pro Ser Asp Ile Ala Val Glu Trp Glu Ser Asn Gly Gln Pro Glu Asn
                260              265              270
Asn Tyr Lys Thr Thr Pro Pro Val Leu Asp Ser Asp Gly Ser Phe Phe
                275              280              285
Leu Tyr Ser Lys Leu Thr Val Asp Lys Ser Arg Trp Gln Gln Gly Asn
    290              295              300
Val Phe Ser Cys Ser Val Met His Glu Ala Leu His Asn His Tyr Thr
305              310              315              320
Gln Lys Ser Leu Ser Leu Ser Pro Gly Lys
                325              330
```

```
<210> SEQ ID NO 18
<211> LENGTH: 990
<212> TYPE: DNA
<213> ORGANISM: Homo sapiens

<400> SEQUENCE: 18
gcctccacca agggcccatc ggtcttcccc ctggcaccct cctccaagag cacctctggg      60
ggcacagcag ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggga     360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacaca     960
cagaagagcc tctccctgtc tccgggtaaa                                       990

<210> SEQ ID NO 19
```

```
<211> LENGTH: 106
<212> TYPE: PRT
<213> ORGANISM: Homo sapiens

<400> SEQUENCE: 19

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 20
<211> LENGTH: 318
<212> TYPE: DNA
<213> ORGANISM: Homo sapiens

<400> SEQUENCE: 20
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gttcgcccgt cacaaagagc     300
ttcaacaggg gagagtgt                                                   318

<210> SEQ ID NO 21
<211> LENGTH: 106
<212> TYPE: PRT
<213> ORGANISM: Homo sapiens

<400> SEQUENCE: 21

Arg Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 22
<211> LENGTH: 318
```

-continued

```
<212> TYPE: DNA
<213> ORGANISM: Homo sapiens

<400> SEQUENCE: 22
cgtcagccca aggctgcccc ctcggtcact ctgttcccac cctcgagtga ggagcttcaa         60
gccaacaagg ccacactggt gtgtctcata agtgacttct acccgggagc cgtgacagtg        120
gcctggaagg cagatagcag ccccgtcaag gcgggagtgg agaccaccac accctccaaa        180
caaagcaaca acaagtacgc ggccagcagc tacctgagcc tgacgcctga gcagtggaag        240
tcccacaaaa gctacagctg ccaggtcacg catgaaggga gcaccgtgga gaagacagtg        300
gcccctacag aatgttca                                                      318
```